US009867527B2

(12) United States Patent
Ide

(10) Patent No.: US 9,867,527 B2
(45) Date of Patent: Jan. 16, 2018

(54) ENDOSCOPE FOGGING PREVENTION HEATER UNIT AND ENDOSCOPE

(71) Applicant: OLYMPUS CORPORATION, Tokyo (JP)

(72) Inventor: Takayuki Ide, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 150 days.

(21) Appl. No.: 14/797,334

(22) Filed: Jul. 13, 2015

(65) Prior Publication Data

US 2015/0313454 A1   Nov. 5, 2015

Related U.S. Application Data

(63) Continuation of application No. PCT/JP2014/050343, filed on Jan. 10, 2014.

(30) Foreign Application Priority Data

Feb. 15, 2013  (JP) .................................. 2013-027645

(51) Int. Cl.
*A61B 1/00*   (2006.01)
*A61B 1/12*   (2006.01)
(Continued)

(52) U.S. Cl.
CPC ............ *A61B 1/128* (2013.01); *A61B 1/0008* (2013.01); *A61B 1/00055* (2013.01);
(Continued)

(58) Field of Classification Search
CPC ....... A61B 1/127; A61B 1/04; A61B 1/00055; A61B 1/0008; A61B 1/128;
(Continued)

(56) References Cited

U.S. PATENT DOCUMENTS

2007/0149856 A1\*  6/2007  Segawa .................. A61B 1/051
                                                   600/169
2010/0105980 A1\*  4/2010  Shimizu ............. A61B 1/00096
                                                   600/101
(Continued)

FOREIGN PATENT DOCUMENTS

JP        H11-295617 A       10/1999
JP        2003-284686 A      10/2003
(Continued)

OTHER PUBLICATIONS

Extended Supplementary European Search Report dated Sep. 16, 2016 received in PCT/JP2014050343.
(Continued)

*Primary Examiner* — Alexandra Newton
*Assistant Examiner* — Genja Williams
(74) *Attorney, Agent, or Firm* — Scully, Scott, Murphy & Presser, P.C.

(57) ABSTRACT

A heater unit includes a heater which is provided inside of a distal end portion of an endoscope insertion portion and which heats the inside to prevent fogging which occurs in an optical member provided the inside, a temperature sensor which measures the temperature of the inside and a flexible substrate. The heater unit further includes an insulating sealing portion which seals a mounting surface of the heater mounted on the flexible substrate, which seals the heater so that so that a joint surface of the heater that faces the mounting surface and that is joined to the lens frame is exposed and which seals the whole temperature sensor.

15 Claims, 5 Drawing Sheets

(51) Int. Cl.
  *G02B 27/00* (2006.01)
  *G02B 23/24* (2006.01)
  *A61B 1/253* (2006.01)
  *A61B 1/04* (2006.01)

(52) U.S. Cl.
  CPC .......... *A61B 1/00096* (2013.01); *A61B 1/127* (2013.01); *G02B 23/2469* (2013.01); *G02B 27/0006* (2013.01); *A61B 1/04* (2013.01); *A61B 1/253* (2013.01)

(58) Field of Classification Search
  CPC ............ A61B 1/00096; G02B 27/0006; G02B 23/2476; G02B 23/2469
  See application file for complete search history.

(56) References Cited

U.S. PATENT DOCUMENTS

2010/0309553 A1* 12/2010 Nagamizu ................ A61B 1/04 359/512
2011/0074941 A1* 3/2011 Takasaki .................. A61B 1/05 348/68

FOREIGN PATENT DOCUMENTS

| JP | 2006-000282 A | 1/2006 |
| WO | WO 2010/055753 A1 | 5/2010 |
| WO | WO 2012/056963 A1 | 5/2012 |
| WO | WO 2013/054819 A1 | 4/2013 |

OTHER PUBLICATIONS

English translation of International Preliminary Report on Patentability dated Aug. 27, 2015 together with the Written Opinion received in related International Application No. PCT/JP2014/050343.

International Search Report dated Apr. 22, 2014 issued in PCT/JP2014/050343.

* cited by examiner

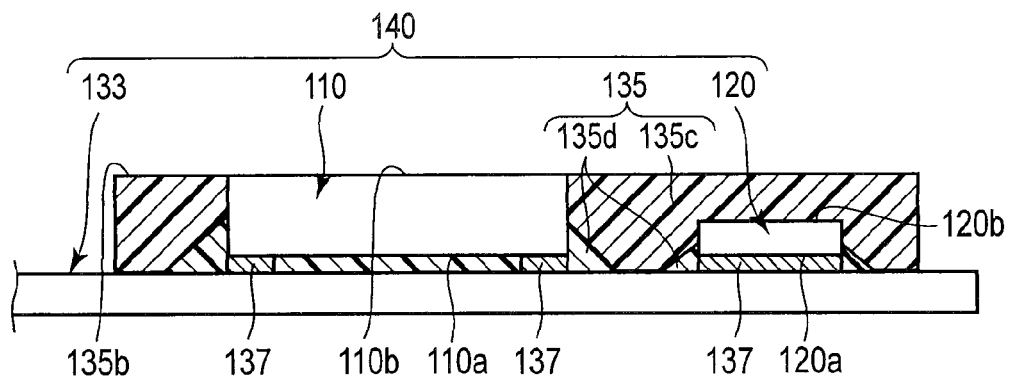
F I G. 6
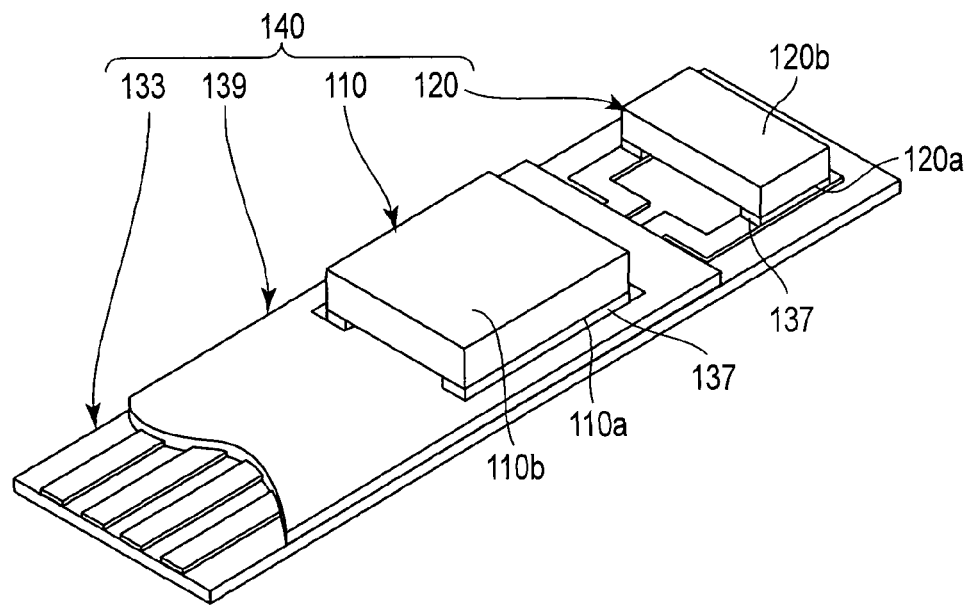
F I G. 7

ENDOSCOPE FOGGING PREVENTION HEATER UNIT AND ENDOSCOPE

CROSS-REFERENCE TO RELATED APPLICATIONS

This application is a Continuation Application of PCT Application No. PCT/JP2014/050343, filed Jan. 10, 2014 and based upon and claiming the benefit of priority from prior Japanese Patent Application No. 2013-027645, filed Feb. 15, 2013, the entire contents of all of which are incorporated herein by reference.

BACKGROUND OF THE INVENTION

1. Field of the Invention

The present invention relates to an endoscope fogging prevention heater unit which prevents fogging which occurs in an endoscope, and an endoscope.

2. Description of the Related Art

A distal end portion of an endoscope insertion portion is inserted in a humid environment, for example, in a body cavity. If the distal end portion is inserted in this environment and the temperature of the inserted distal end portion is lower than the temperature of the environment, the surface of an optical member (e.g. a lens cover) provided in the distal end portion may fog because of a temperature difference. This fog may prevent, for example, an observation or a treatment.

Thus, to counter such fog, the endoscope has a fogging prevention heater unit which is provided inside of the distal end portion of the insertion portion and which prevents the fog. This fogging prevention heater unit has a heater which heats the inside to prevent fogging, a temperature sensor which measures the temperature of the inside, and a substrate on which the heater and the temperature sensor are mounted.

Such a fogging prevention heater unit has been disclosed in, for example, Jpn. Pat. Appln. KOKAI Publication No. 2006-282. In Jpn. Pat. Appln. KOKAI Publication No. 2006-282, heating by the heater is controlled on the basis of the temperature which the temperature sensor detects.

BRIEF SUMMARY OF THE INVENTION

An aspect of an endoscope fogging prevention system of the present which is provided inside of a distal end portion of an endoscope insertion portion and which prevents fogging which occurs in an optical member provided the inside, the endoscope fogging prevention heater unit including a heating section which heats the inside to prevent the fogging, a temperature measurement section which measures the temperature of the inside, an identical wiring substrate portion on which the heating section and the temperature measurement section are mounted and an insulating sealing portion which seals a mounting surface of the heating section mounted on the wiring substrate portion, which seals the heating section so that an opposite surface facing the mounting surface is exposed and which seals the whole temperature measurement section.

An aspect of an endoscope of the present includes the endoscope fogging prevention system.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 6 is a diagram showing the configuration of a heater unit according to a second embodiment; and FIG. 7 shows a third embodiment, and is a perspective view of a heater unit except for the sealing portion.

DETAILED DESCRIPTION OF THE INVENTION

Hereinafter, embodiments of the present invention will be described in detail with reference to the drawings.

[First Embodiment]

[Configuration]

The first embodiment is described with reference to FIG. 1, FIG. 2, FIG. 3, FIG. 4A, FIG. 4B, FIG. 4C, FIG. 5A, and FIG. 5B. In some of the drawings, components are not shown for clarity of diagrammatic representation. Also, for example, in FIG. 4A, a heater 110 and a temperature sensor 120 are shown in a simplified manner.

[Configuration of Distal End Portion 10a of Endoscope]

Figure 1:
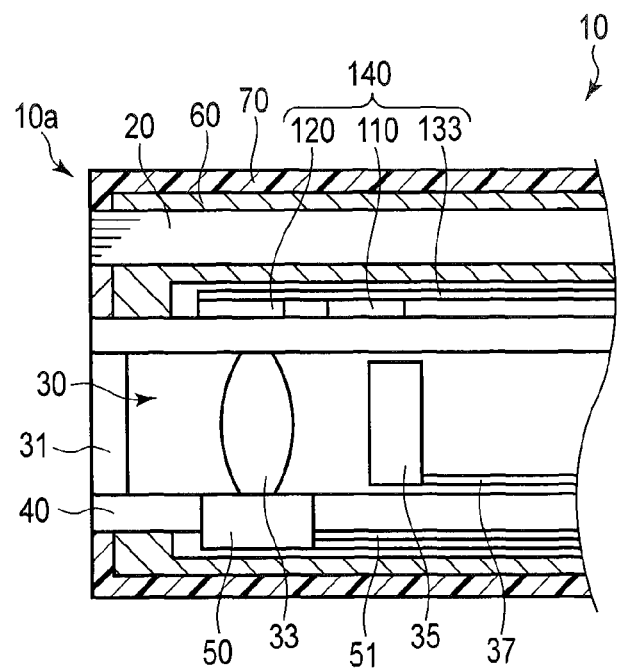
FIG. 1 is a diagram showing the internal structure of a distal end portion of an insertion portion of an endoscope according to the present invention.

As shown in FIG. 1, an unshown endoscope has a hollow and elongated insertion portion 10 to be inserted into a lumen such as a body cavity. A distal end portion 10a of the insertion portion 10 has a light guide 20 which guides illumination light to apply the illumination light to an observation target, and an imaging unit 30 which images the observation target. The distal end portion 10a further has a lens frame 40 which holds the imaging unit 30, and a driver element 50 which is provided in the lens frame 40 and which drives a lens 33 of the imaging unit 30 to perform focusing or zooming.

The light guide 20 is connected to an unshown light source apparatus through the insertion portion 10 and an unshown operation portion of the endoscope so that the light is supplied to the light guide 20. The light guide 20 then emits the illumination light to the outside from the distal end portion of the light guide 20.

The imaging unit 30 has a lens cover 31 provided inside of the distal end portion 10a to be exposed to the outside from the distal face of the distal end portion 10a, and the lens 33 provided behind the lens cover 31. The imaging unit 30 further has an image pickup device 35 provided behind the lens 33, and an imaging cable 37 which is connected to the image pickup device 35 and which supplies electric power to the image pickup device 35, and which sends a control signal to control the image pickup device 35 to the image pickup device 35 and transmits a video signal obtained by the image pickup device 35.

The imaging cable 37 is inserted into a connector via the insertion portion 10, the operation portion, and an universal cord. This connector is connected to an unshown control device which controls the endoscope, and the imaging cable 37 is thereby connected to the control device. Thus, the electric power and the control signal to drive the image pickup device 35 are supplied to the imaging cable 37. The imaging cable 37 then supplies and sends the electric power and the control signal to the image pickup device 35. This connector is connected to the control device so that the video signal obtained by the image pickup device 35 is transmitted to the control device.

The lens cover 31 may have a form of a lens instead of being only a plate-shaped cover member. In the following explanation, at least one of the lens cover 31 and the lens 33 at the distal end portion 10a which is prevented from fogging when the distal end portion 10a is inserted in, for example, a body cavity is referred to as an optical member. The optical member has only to be provided, for example, inside of the distal end portion 10a to be exposed to the outside from the distal face of the distal end portion 10a.

The driver element 50 has, for example, a motor. The driver element 50 is connected to a driver cable 51 which supplies the electric power to the driver element 50 and which sends a control signal to the driver element 50 to control the driver element 50.

The driver cable 51 is inserted into the connector via the insertion portion 10, the operation portion, and the universal cord. This connector is connected to the unshown control device so that the driver cable 51 is connected to the control device. Thereby, the electric power and the control signal to drive the driver element 50 are supplied to the driver cable 51. The driver cable 51 then supplies the electric power and the control signal to the driver element 50.

The lens frame 40 is formed by, for example, a circular cylindrical member. The lens frame 40 houses the imaging unit 30 in the circular cylinder.

As shown in FIG. 1, the distal end portion 10a further has an inner frame 60 which holds the light guide 20 and the lens frame 40, and an outer frame 70 which covers the inner frame 60 and which is formed as an outermost layer of the distal end portion 10a.

The inner frame 60 is made of, for example, a metal, and the outer frame 70 is made of, for example, a resin.

[Fogging of Optical Member]

The endoscope having the above-mentioned distal end portion 10a is normally placed under an environment at controlled temperature and humidity, for example, in a treatment room. Thus, the distal end portion 10a is exposed to such temperature and humidity before use. When the insertion portion 10 is inserted into the body cavity, the optical member such as the lens cover 31 fogs due to, for example, the temperature difference between the room temperature and the body temperature or a high-humidity environment (a humidity of about 98% to about 100%) inside the body, and the imaging field of view significantly deteriorates.

[Configuration 1 of Endoscope Fogging Prevention System 100 (Heater Unit 140)]

Figure 2:
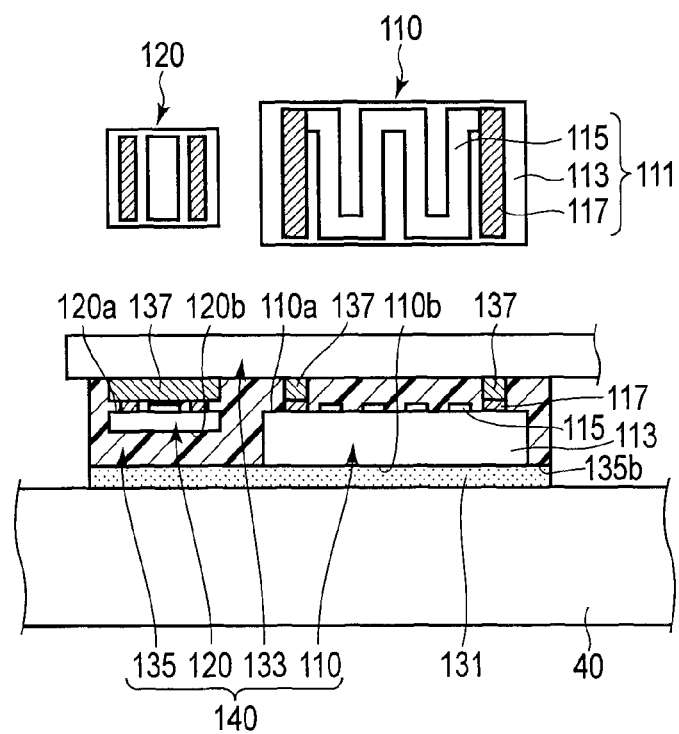
FIG. 2 is a diagram showing the structure of a heater unit.
Figure 3:
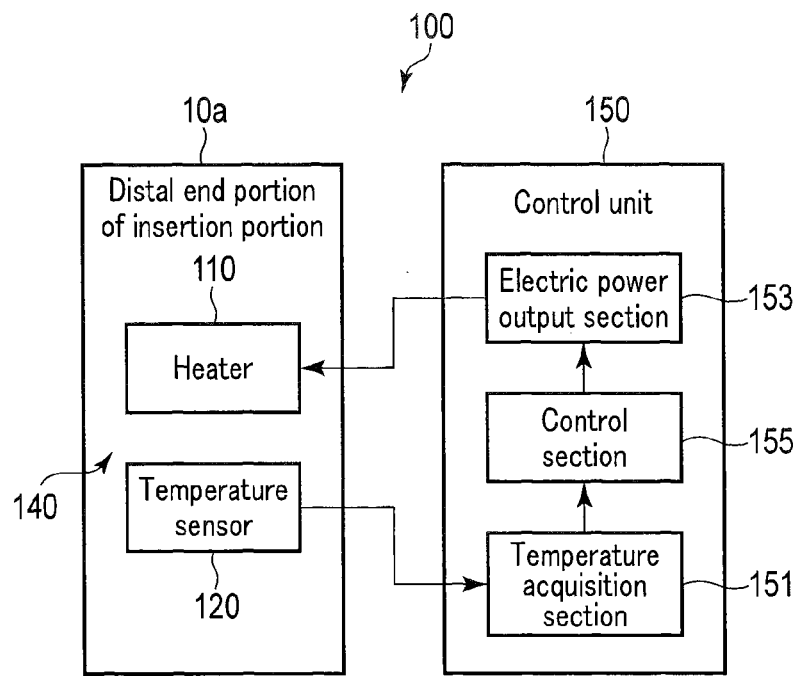
FIG. 3 is a diagram showing configurations 1 and 2 of an endoscope fogging prevention system according to a first embodiment.

Thus, as shown in FIG. 1, FIG. 2, and FIG. 3, the endoscope and the unshown control device which controls the endoscope are equipped with an endoscope fogging prevention system 100 to prevent the fogging which occurs in the endoscope. The endoscope fogging prevention system 100 has an endoscope fogging prevention heater unit (hereinafter referred to as a heater unit 140) which is provided inside of the distal end portion 10a of the insertion portion 10 and which prevents the fogging which occurs in the optical member provided inside of the distal end portion 10a.

The heater unit 140 has the heater 110 which is provided in, for example, the lens frame 40 and which is included in a heating section for heating the inside of the distal end portion 10a including the lens cover 31 via the lens frame 40 to prevent the fogging which occurs in an optical member such as the lens cover 31, and a temperature sensor 120 which is provided in, for example, the lens frame 40 and which is a temperature measurement section for measuring the temperature inside of the distal end portion 10a including the lens cover 31 via the lens frame 40. The heater unit 140 further has a flexible substrate 133 that is an identical wiring substrate portion on which the heater 110 and the temperature sensor 120 are mounted.

As shown in FIG. 2, for example, a rear surface of the heater unit 140 is joined to, for example, an outer circumferential surface of the lens frame 40 by, for example, an adhesive agent 131 having high heat conductivity. The adhesive agent 131 may have a configuration in which an adhesive agent having low heat conductivity is applied extremely thinly. As shown in FIG. 1, the heater 110 and the temperature sensor 120 have only to be provided inside of the distal end portion 10a. Thus, the heater 110 and the temperature sensor 120 may be provided in, for example, the inner frame 60 for holding a lens unit. The lens unit includes, for example, the lens cover 31, the lens 33, and the lens frame 40 which holds these components. As shown in FIG. 1 and FIG. 2, the heater 110 and the temperature sensor 120 are mounted on the flexible substrate 133 by, for example, surface-mount technology. The flexible substrate 133 is connected to an unshown cable which supplies the electric power and the control signal to the heater 110 and the temperature sensor 120 via the flexible substrate 133 and which transmits detection data detected by the temperature sensor 120. This cable is inserted into the connector via the insertion portion 10, the operation portion, and the universal cord. This connector is connected to the control device so that the cable is connected to the control device. Thus, the electric power and the control signal to drive the heater 110 and the temperature sensor 120 are supplied to the heater 110 and the temperature sensor 120. The cable then supplies the electric power and the control signal to the heater 110 and the temperature sensor 120. Moreover, this connector is connected to the control device so that temperature data included in the detection data detected by the temperature sensor 120 is transmitted to the control device.

As shown in FIG. 1 and FIG. 2, for example, the heater 110 is provided adjacent to the temperature sensor 120 in a longitudinal axis direction of the distal end portion 10a. For example, the heater 110 is provided a desired distance apart from the temperature sensor 120. For example, the heater 110 is provided farther from the lens cover 31 (the surface of the distal end portion 10a) than the temperature sensor 120. The positions where the heater 110 and the temperature sensor 120 are provided may be reversed. The positional relation between the heater 110 and the temperature sensor 120 is not particularly limited.

[Heater 110]

The heater 110 heats the inside of the distal end portion 10a, for example, to such a temperature that the lens cover 31 is higher than the body temperature and that a living tissue is not burned. This temperature is, for example, about 38° C. or more and 42° C. or less. The heater 110 heats the inside of the distal end portion 10a so that the optical member will be set to this temperature. The heater 110 may directly heat the optical member or indirectly heat the optical member via, for example, the lens frame 40 or the inner frame 60.

As shown in FIG. 2, the heater 110 has, for example, a heating chip 111. This heating chip 111 has, for example, a ceramic substrate 113, a metallic resistance 115 provided on the substrate 113, and a pad 117 which is provided on the substrate 113 and which is electrically connected to the metallic resistance 115. The metallic resistance 115 is formed into a thin film shape or a paste state, and functions as a heating element. The pad 117 is formed as an electric current introduction terminal.

[Temperature Sensor 120]

The temperature sensor 120 measures the temperature inside of the distal end portion 10a. The temperature sensor 120 is formed by a ceramic substrate as a base in the same manner as the heating chip 111, or by temperature sensor chip such as a thermistor comprising a bulk.

[Configuration 2 of Endoscope Fogging Prevention System 100 (Control Unit 150)]

As shown in FIG. 3, the fogging prevention system 100 further has a control unit 150 which controls the driving of the heater 110 based on the temperature inside of the distal end portion 10a measured by the temperature sensor 120. The control unit 150 is, for example, separate from the endoscope. The control unit 150 is connected to, for example, the universal cord of the endoscope, and is provided in an unshown control device which controls the endoscope.

As shown in FIG. 3, the control unit 150 has a temperature acquisition section 151 which acquires the actual temperature inside of the distal end portion 10a measured by the temperature sensor 120, and an electric power output section 153 which outputs, to the heater 110, electric power (hereinafter referred to as heater driving electric power) necessary for the driving of the heater 110.

As shown in FIG. 3, the control unit 150 also has a control section 155 which calculates the difference between the temperature acquired by the temperature acquisition section 151 and a preset target temperature, calculates heater driving electric power that eliminates the difference based on the calculated difference, and controls the electric power output section 153 so that the electric power output section 153 outputs the calculated heater driving electric power to the heater 110. The target temperature has, for example, a temperature that prevents the fogging of the optical member such as the lens cover 31 by heating the optical member. The target temperature also has a temperature less than or equal to the temperature at which the temperature in the outer frame 70 that is an outermost part of the distal end portion 10a, in particular, the temperature in the vicinity of the heater 110 does not burn the living tissue. The target temperature can be, for example, suitably adjusted in a desired manner by, for example, the control unit 150. The target temperature is previously recorded in, for example, an unshown recording section provided in the control unit 150. The temperature which is an acquisition result acquired by the temperature acquisition section 151 is recorded in the unshown recording section. The temperature acquisition section 151 acquires, for example, desired timing or a desired period, and the temperature.

The temperature measured by the temperature sensor 120 is fed back to the control unit 150. The temperature inside of the distal end portion 10a is accurately controlled by the repetition of the feedback so that the heating temperature of the heater 110 will be set to the desired temperature. The control method of the heater 110 is, for example, on-off control, PWM control, or PID control.

[Heat Conductivity and Insulating Properties of Heater Unit 140]

In the above-mentioned feedback, the heat conductivity between the heater unit 140 and the inside of the distal end portion 10a is an important factor in the accurate control of the temperature inside of the distal end portion 10a.

Under such circumstances, when, for example, a surgical endoscope is used together with an unshown treatment instrument which treats an affected part by an electrical action, there is a possibility that the heater unit 140 may be affected by static electricity, etc, from the outside of the heater unit 140, for example, from the treatment instrument. Thus, there is a risk that the performance of the heater unit 140, for example, temperature control performance may deteriorate due to the static electricity. Accordingly, the heater unit 140 needs to increase resistance to the static electricity, and therefore needs to have insulating properties.

Figure 4A:
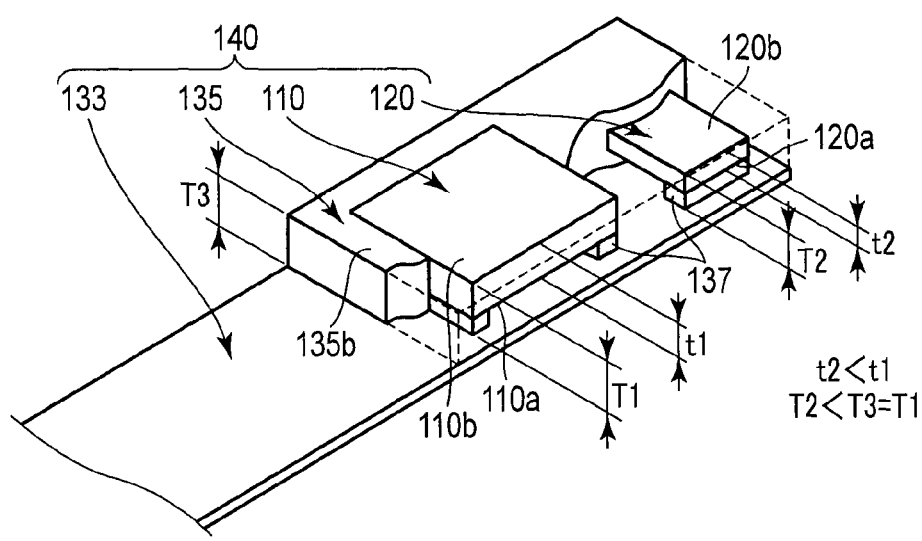
FIG. 4A is a perspective view of the heater unit in which part of a sealing portion is transmitted, and is a diagram showing the relation between thickness $t1$ of a heater, thickness $t2$ of a temperature sensor, thickness $T1$ of the heater including a joint material, thickness $T2$ of the temperature sensor including the joint material, and thickness $T3$ of the sealing portion.
Figure 5A:
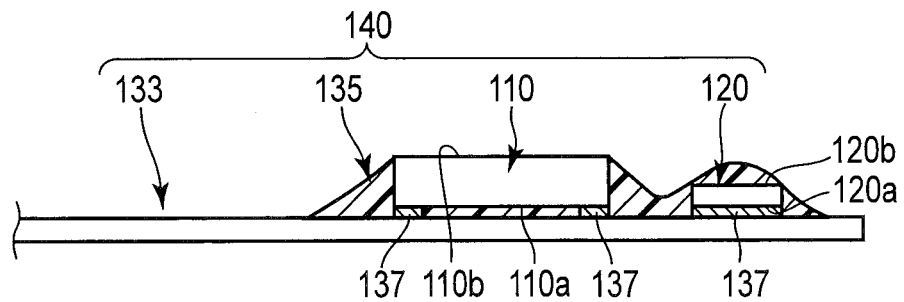
FIG. 5A is a diagram showing the configuration of the heater unit having the sealing portion in which the thickness is non-uniform.
Figure 5B:
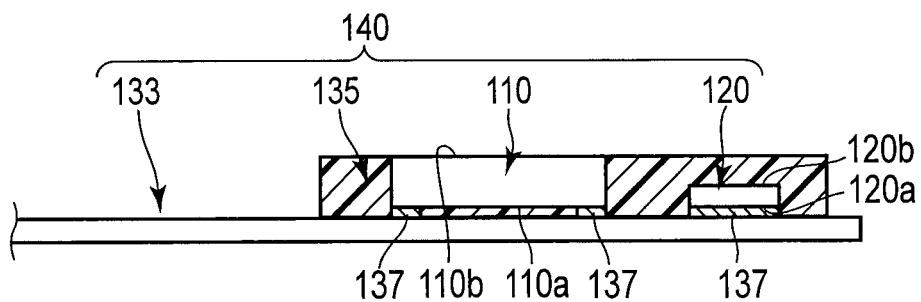
FIG. 5B is a diagram showing the configuration of the heater unit having the sealing portion in which the thickness is uniform.

As shown in FIG. 2, FIG. 4A, and FIG. 5B, in view of the above-mentioned heat conductivity and insulating properties, the heater unit 140 also has an insulating sealing portion 135 which seals a mounting surface 110a of the heater 110 mounted on the flexible substrate 133, which seals the heater 110 so that a joint surface 110b of the heater 110 that faces the mounting surface 110a and that is joined to the lens frame 40 is exposed and which seals the whole temperature sensor 120 so that the temperature sensor 120 is buried. As shown in FIG. 2 and FIG. 5B, the sealing portion 135 seals the heater 110 and the temperature sensor 120, and is mounted on the flexible substrate 133. In the sealing portion 135, the temperature sensor 120 is buried in the sealing portion 135.

This sealing portion 135 is made of, for example, an epoxy resin to ensure insulating resistance of the sealing portion 135 and the volume resistivity of the sealing portion 135 considering that the sealing portion 135 that has cured functions as a solid structure. The heat conductivity of the sealing portion 135 is low.

As shown in FIG. 2, FIG. 4A, and FIG. 5B, the heater 110 sealed by the sealing portion 135 except for the joint surface 110b has, for example, a rectangular-column shape. As shown in FIG. 2, FIG. 4A, FIG. 4B, FIG. 5A, and FIG. 5B, this heater 110 has the mounting surface 110a that is mounted on the flexible substrate 133, and the joint surface 110b which is provided to face the mounting surface 110a, which is exposed from the sealing portion 135 so that the adhesive agent 131 is applied thereto and which is joined to the outer circumferential surface of the lens frame 40 by the adhesive agent 131. For example, the mounting surface 110a is the bottom surface of the heater 110, and the joint surface 110b is the top surface of the heater 110, is an opposite surface facing the mounting surface 110a, and is an outer layer surface. The mounting surface 110a and the joint surface 110b are, for example, flat surfaces. The circumferential surface of the heater 110 is also sealed by the sealing portion 135.

As shown in FIG. 2, FIG. 4A, and FIG. 5B, the temperature sensor 120 which is entirely sealed by the sealing portion 135 has, for example, a rectangular-column shape thinner than the heater 110. The temperature sensor 120 has a mounting surface 120a which is mounted on the flexible substrate 133, and an opposite surface 120b which is provided to face the mounting surface 120a. For example, the mounting surface 120a is the bottom surface of the temperature sensor 120, and the opposite surface 120b is the top surface of the temperature sensor 120. The mounting surface 120a and the opposite surface 120b are, for example, flat surfaces.

Figure 4B:
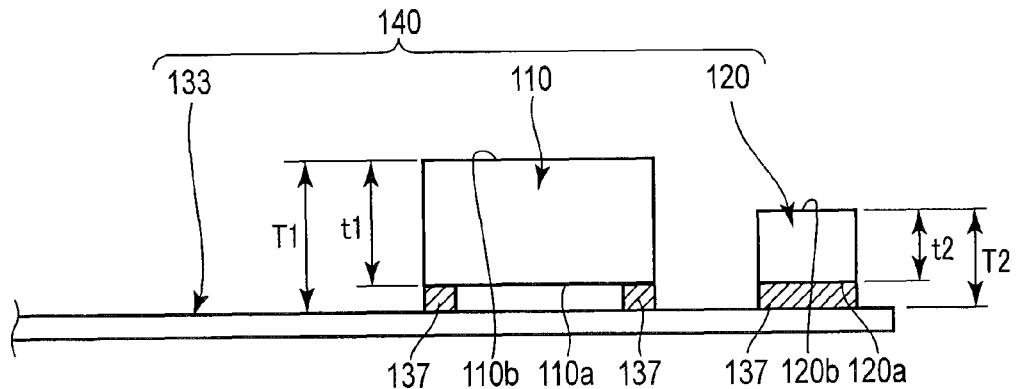
FIG. 4B is a diagram showing the relation between the thickness $t1$ of the heater and the thickness $t2$ of the temperature sensor, and the relation between the thickness $T1$ of the heater including the joint material and the thickness $T2$ of the temperature sensor including the joint material.

As shown in FIG. 4A and FIG. 4B, in the heater 110 and the temperature sensor 120, the mounting surface 110a is joined to the flexible substrate 133 by a joint material 137 such as solder, and the mounting surface 120a is joined to the flexible substrate 133 by a joint material 137 such as solder. Thus, the heater 110 is electrically connected to the flexible substrate 133, and the temperature sensor 120 is also electrically connected to the flexible substrate 133. Both the joint materials 137 have the same height so that the mounting surface 110a and the mounting surface 120a that are mounted are provided flush with each other and so that the joint surface 110b is provided farther from the flexible substrate 133 than the opposite surface 120b.

As shown in FIG. 4B, thickness t1 of the heater 110 is larger than thickness t2 of the temperature sensor 120, and there is a height difference between the heater 110 and the temperature sensor 120.

In the sealing portion 135 made of an epoxy resin, the dielectric breakdown strength of the sealing portion 135 is, for example, about 20 kV/mm to about 30 kV/mm. The temperature sensor 120 has a dielectric breakdown resistance of several kV, so that, for example, the heater 110 is about 0.05 mm or more thicker than the temperature sensor 120 when the heater 110 and the temperature sensor 120 are mounted on the flexible substrate 133.

Figure 4C:
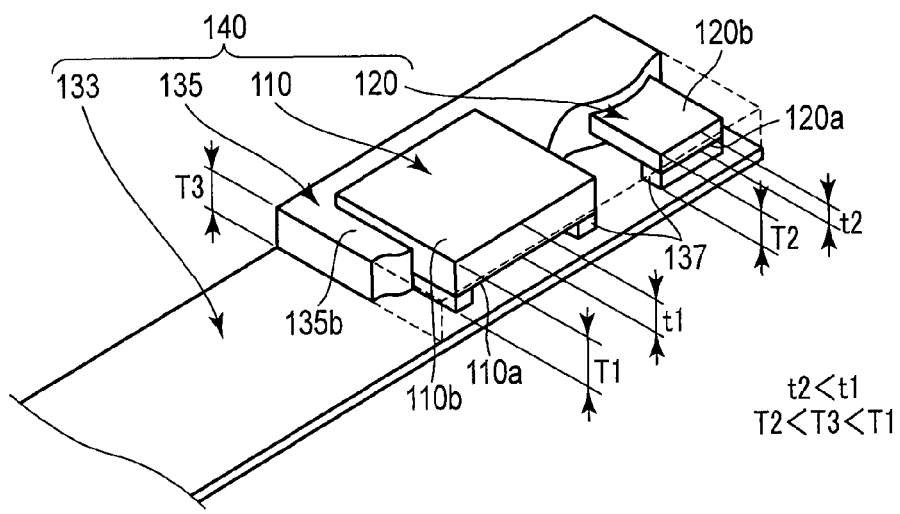
FIG. 4C is a perspective view of the heater unit in which part of a sealing portion is transmitted, and is a diagram showing the relation between the thickness $t1$ of the heater, the thickness $t2$ of the temperature sensor, the thickness $T1$ of the heater including the joint material, the thickness $T2$ of the temperature sensor including the joint material, and the thickness $T3$ of the sealing portion.

As shown in FIG. 4A, FIG. 4B, and FIG. 4C, the relation between thickness T1 of the heater 110 including the joint material 137, the thickness T2 of the temperature sensor 120 including the joint material 137, and the thickness T3 of the sealing portion 135 is as follows:

$$T2 < T3 \leq T1 \quad \text{Equation (1)}$$

Thus, in the sealing portion 135, the joint materials 137, and the heater 110 that are mounted on the flexible substrate 133, a flat top surface 135b of the sealing portion 135 is provided flush with the joint surface 110b as shown in FIG. 4A, or provided lower than the joint surface 110b and on the side of the flexible substrate 133 as shown in FIG. 4C. In other words, the joint surface 110b is provided flush with the top surface 135b of the sealing portion 135 as shown in FIG. 4A, or provided higher than the top surface 135b of the sealing portion 135 and apart from the flexible substrate 133 as shown in FIG. 4C, in an exposed state.

When, for example, the sealing portion 135 is formed by stamping to fulfill Equation (1) above, the sealing portion 135 having non-uniform thickness is formed because of the wettability of the sealing portion 135, as shown in FIG. 5A. If the thickness of the sealing portion 135 is varied, there is a risk that the thickness of the sealing portion 135 may be thinner, for example, at the corners of the temperature sensor 120 than in other parts and sufficient insulating properties may not be ensured in the heater unit 140.

For example, a embankment member serving as a frame formed by photolithography or stamping is used to fulfill Equation (1) above and ensure sufficient insulating properties. This embankment member is mounted on the flexible substrate 133 to surround the heater 110 and the temperature sensor 120 in advance. In this state, as shown in FIG. 5B, the sealing portion 135 is poured into the embankment member and cured, and is thereby mounted on the flexible substrate 133.

Alternatively, a non-adhesive material such as a non-adhesive sheet or tape may be used as the embankment member. In this case, the embankment member is provided on or bonded to the flexible substrate 133 to surround the heater 110 and the temperature sensor 120 in advance. In this state, the sealing portion 135 is poured into the non-adhesive material and cured, and is thereby mounted on the flexible substrate 133.

Alternatively, for example, a frame-shaped die previously formed into the shape of the cured sealing portion 135 may be used. The die is mounted on the flexible substrate 133 to surround the heater 110 and the temperature sensor 120. In this state, the sealing portion 135 is poured into the die and cured, and is thereby mounted on the flexible substrate 133.

Consequently, the sealing portion 135 having a uniform thickness as shown in FIG. 4A, FIG. 4C and FIG. 5B and which ensures sufficient insulating properties and which fulfills Equation (1) above is formed.

[Operation Method]

An operation method according to the present embodiment is described below.

[Heater 110]

When the heater unit 140 heats the inside of the distal end portion 10a, the heat flux from the heater 110 into the distal end portion 10a is significantly high. Here, when the sealing portion 135 having low heat conductivity is inadvertently provided between the heater 110 and the distal end portion 10a, the temperature difference between the heater 110 and the distal end portion 10a increases. Therefore, the temperature of the heater 110 excessively rises when the inside of the distal end portion 10a reaches a desired temperature. In this respect, there is a risk that the characteristics of the heater 110 may deteriorate or the above-mentioned target temperature may not be maintained.

Therefore, in the present embodiment, as described above, the sealing portion 135 seals the heater 110 so that the joint surface 110b is exposed and so that the joint surface 110b is joined to the outer circumferential surface of the lens frame 40 by the adhesive agent 131 having high heat conductivity or by the adhesive agent 131 which has low heat conductivity and which has a configuration to be applied extremely thin. Thus, the heater 110 heats the inside of the distal end portion 10a including the lens frame 40 and optical lenses via the joint surface 110b. Accordingly, an excessive rise in the temperature of the heater 110 is prevented, deterioration of the characteristics of the heater 110 is prevented, and the target temperature is maintained.

Moreover, the decrease of heat conductivity between the heater 110 and the inside of the distal end portion 10a heated by the heater 110 is prevented by the exposed joint surface 110b. That is, the heat generated by the heater 110 is efficiently transmitted to the inside of the distal end portion 10a.

Most of the heater 110 is sealed by the sealing portion 135 except for the joint surface 110b. Therefore, the heater 110 ensures desired insulating properties, and the resistance of the heater 110 to static electricity increases. The heater 110 is not affected by external static electricity, etc, and ensures desired performance.

Thus, both heat conductivity and insulating properties are achieved in the heater 110.

[Temperature Sensor 120]

When the heater unit 140 heats the inside of the distal end portion 10a, the heat flux from the inside of the distal end portion 10a into the temperature sensor 120 is lower than the heat flux in the heater 110 described above. Thus, even if the sealing portion 135 having low heat conductivity intervenes between the temperature sensor 120 and the inside of the distal end portion 10a, the temperature difference between the temperature sensor 120 and the inside of the distal end portion 10a is small. Therefore, even if the temperature sensor 120 is buried in the sealing portion 135 as in the present embodiment, the sealing portion 135 has a small effect on the measurement accuracy of the temperature sensor 120 when the temperature sensor 120 measures the temperature inside of the distal end portion 10a. Consequently, even if the heat conductivity between the temperature sensor 120 and the inside of the distal end portion 10a heated by the heater 110 has decreased to some degree, the effect on the temperature control of the distal end portion 10a is small.

The temperature sensor 120 is sealed by the sealing portion 135 to be buried in the sealing portion 135. Therefore, the temperature sensor 120 ensures desired insulating properties, and the resistance of the heater 110 to static electricity increases. The temperature sensor 120 is not affected by external static electricity, etc, and ensures desired performance.

Thus, both heat conductivity and insulating properties are achieved in the temperature sensor 120.

As in the present embodiment, the temperature measured by the temperature sensor 120 is fed back to the control unit. When the heating temperature of the heater 110 is set to the desired temperature by the repetition of the feedback, temperature controllability inside of the distal end portion 10a is not affected within the driving capacity of the control section even if the characteristics of the heater 110 (e.g. the resistance value of the metallic resistance 115) are slightly changed by, for example, static electricity. However, the temperature sensor 120 desirably has a high resistance temperature coefficient to improve the temperature measurement accuracy. Thus, the temperature sensor 120 is subject to a characteristic change attributed to, for example, static electricity, and the temperature controllability inside of the distal end portion 10a is directly affected if the characteristics of the temperature sensor 120 change. In view of this, the temperature sensor 120 is sealed by the sealing portion 135 to be buried in the sealing portion 135, as described above.

Consequently, both heat conductivity and insulating properties are achieved in the heater unit 140.

[Advantageous Effects]

Thus, according to the present embodiment, the sealing portion 135 seals the heater 110 so that the joint surface 110b is exposed, and seals the whole temperature sensor 120 so that the temperature sensor 120 is buried in the sealing portion 135. As a result, in the present embodiment, it is possible to provide the endoscope fogging prevention heater unit 140 in which both heat conductivity and insulating properties are achieved. Especially in the present embodiment, it is possible to ensure heat conductivity such that the heat generated by the heater 110 is efficiently transmitted to the inside of the distal end portion 10a, the temperature sensor 120 can ensure desired insulating properties, the resistance of the temperature sensor 120 to static electricity can be increased, and it is possible to prevent the temperature sensor 120 from being affected by external static electricity, etc, from the outside. Moreover, in the present embodiment, the heater unit 140 can achieve both heat conductivity and insulating properties by itself without being affected by the insulating properties or the like of other members.

Furthermore, according to the present embodiment, the thickness t1 of the heater 110 is larger than the thickness t2 of the temperature sensor 120, so that the joint surface 110b can be easily exposed.

Furthermore, according to the present embodiment, the relation $T2<T3 \leq T1$ is satisfied, so that it is possible to seal the heater 110 and reliably expose the joint surface 110b at the same time, seal the temperature sensor 120, and certainly achieve both heat conductivity and insulating properties.

Furthermore, according to the present embodiment, the sealing portion 135 is made of an epoxy resin, so that it is possible to ensure the insulating resistance of the sealing portion 135 and the volume resistivity of the sealing portion 135, and the cured sealing portion 135 can function as a structure.

Furthermore, according to the present embodiment, it is possible to provide the endoscope having the heater unit 140 described above.

[Second Embodiment]

[Configuration]

The present embodiment is described with reference to FIG. 6. The configurations different from the configurations according to the first embodiment are only described below.

[Sealing Portion 135]

In general, if voids are generated in the sealing portion 135, the insulating properties of the sealing portion 135 deteriorate, and the sealing portion 135 is more likely to cause a structural defect due to a heat load produced by the increase and decrease of the temperature.

Voids tend to be generated in the lower part of the heater 110 and the lower part of the temperature sensor 120. If voids are generated around the joint material 137, the heater 110 and the temperature sensor 120 are increasingly apt to be directly affected by static electricity, etc.

Thus, the sealing portion 135 according to the present embodiment has adhesive members 135c and 135d different in viscosity from each other, or adhesive members 135c and 135d different in particle diameter from each other before curing. The use of the adhesive member 135c high in viscosity and the adhesive member 135d low in viscosity is described below by way of example.

When the sealing portion 135 seals, the adhesive member 135c covers the adhesive member 135d so that the adhesive member 135c includes the adhesive member 135d. The adhesive member 135d is provided in the vicinity of the joint material 137, in the vicinity of the mounting surface 110a, and in the vicinity of the mounting surface 120a. The adhesive member 135d infiltrates into between the mounting surface 110a, the mounting surface 120a, and the flexible substrate 133 due to a capillary phenomenon.

If the adhesive member 135d is used, the sealing portion 135 is more apt to flow into a clearance portion formed between the non-adhesive material or the die and the flexible substrate 133, and there is a risk that the adhesive member 135d may leak out in unnecessary parts.

Thus, according to the present embodiment, as a first step, the adhesive member 135d is formed by, for example, stamping in the vicinity of a junction. As a second step, the adhesive member 135c covers the adhesive member 135d so that the sealing portion 135 which has a uniform thickness and which ensures sufficient insulating properties and which fulfills Equation (1) above is formed.

In addition, advantageous effects similar to those described above can be obtained even when the adhesive member 135c having a large particle diameter and the adhesive member 135d having a small particle diameter are used.

[Advantageous Effects]

According to the present embodiment, the adhesive member 135d is used, so that the adhesive member 135d can infiltrate into between the mounting surface 110a, the mounting surface 120a, and the flexible substrate 133 due to the capillary phenomenon, and the generation of voids in the sealing portion 135 can be reduced. As a result, in the present embodiment, it is possible to provide the endoscope fogging prevention heater unit 140 in which deterioration of the insulating properties of the sealing portion 135 can be prevented and in which occurrence of a structural defect associated with a heat load can be prevented and in which both heat conductivity and insulating properties are achieved.

Although two kinds of adhesive members 135c and 135d different from each other in viscosity and particle diameter are used in the present embodiment, it is not necessary to limit the kinds of adhesive materials to two kinds as long as one of the adhesive materials higher in viscosity or larger in particle diameter covers the other adhesive material lower in viscosity or smaller in particle diameter.

[Third Embodiment]
[Configuration]

The present embodiment is described with reference to FIG. 7. The configurations different from the configurations according to the first embodiment are only described below. Note that in FIG. 7, some components such as the sealing portion 135 are not shown for clarity of representation.

[Protective Film 139]

The heater unit 140 also has a protective film 139 formed in at least part of the surface of the flexible substrate 133 on which the mounting surface 110a is mounted, except for the surface of the flexible substrate 133 on which the temperature sensor 120 is mounted. The protective film 139 formed except on the surface of the flexible substrate 133 on which the temperature sensor 120 is mounted is formed substantially in the entire surface layer region of the flexible substrate 133.

The protective film 139 ensures the insulation of wiring patterns formed on the flexible substrate 133, and also prevents a short circuit between the wiring patterns caused by the protrusion of the joint material 137.

[Advantageous Effects]

When the protective film 139 is formed on the surface of the flexible substrate 133 immediately under the heater 110 and the temperature sensor 120, the length from the rear surface of the flexible substrate 133 to the joint surface 110b which is the thickness of the entire heater unit 140 is greater if the fulfillment of Equation (1) is taken into consideration.

However, in the present embodiment, the protective film 139 is provided as described above, so that it is possible to ensure the insulation of the wiring patterns formed on the flexible substrate 133, and also to prevent a short circuit between the wiring patterns caused by the protrusion of the joint material 137. At the same time, it is possible to fulfill Equation (1) above, and also prevent the increase of the thickness of the entire heater unit 140.

The present invention is not completely limited to the embodiments described above, and modifications of components can be made at the stage of carrying out the invention without departing from the spirit thereof. Further, various inventions can be made by properly combining the components disclosed in the embodiments described above.

The present invention is not completely limited to the embodiments described above, and modifications of components can be made at the stage of carrying out the invention without departing from the spirit thereof. Further, various inventions can be made by properly combining the components disclosed in the embodiments described above.

What is claimed is:

1. An endoscope fogging prevention heater apparatus which is provided inside of a distal end portion of an endoscope insertion portion and which prevents fogging which occurs in an optical member provided on the inside, the endoscope fogging prevention heater apparatus comprising:
   a heater which heats the inside to prevent the fogging;
   a temperature measurement sensor which measures the temperature of the inside;
   a wiring substrate on which the heater and the temperature measurement sensor are mounted in common; and
   an insulator which seals a mounting surface of the heater mounted on the wiring substrate, which seals the heater so that a surface of the heater opposite to the mounting surface is exposed and which entirely seals the temperature measurement sensor; and
   a conductive element provided inside the distal end portion of the endoscope insertion portion, the conductive element forming a space in optical communication with the optical member inside the distal end portion;
   wherein the surface of the heater is free of the insulator such that the surface is at least indirectly in contact with the conductive element so as to conduct heat from the heater to the conductive element; and
   the surface of the heater is fixed to the conductive element by an adhesive.

2. The endoscope fogging prevention heater apparatus according to claim 1, wherein the insulator comprises a plurality of adhesive members that have different viscosities or different particle diameters from each other before curing.

3. The endoscope fogging prevention heater apparatus according to claim 2, wherein one of the plurality of adhesive materials covers another of the plurality of adhesive materials which has a lower viscosity or smaller particle diameter than the one of the adhesive materials.

4. The endoscope fogging prevention heater apparatus according to claim 1, wherein a dimension of the heater as measured in a height direction from the mounting surface to the surface is greater than a dimension of the temperature measurement sensor in the height direction.

5. The endoscope fogging prevention heater apparatus according to claim 1, wherein a relation $T2<T3 \leq T1$ is satisfied, wherein:

T1 being a dimension of the heater including a joint material which joins the heater to the wiring substrate, the dimension being measured in a height direction from the mounting surface to the surface, T2 being a dimension of the temperature measurement sensor in the height direction, the dimension of the temperature measurement sensor including the joint material which joins the temperature measurement sensor to the wiring substrate, and T3 being the dimension of the insulator in the height direction.

6. The endoscope fogging prevention heater apparatus according to claim 1, wherein a dimension of the heater as measured in a height direction from the mounting surface to the surface is at least about 0.05 mm larger than a dimension of the temperature measurement sensor in the height direction.

7. The endoscope fogging prevention heater apparatus according to claim 1, wherein the insulator is made of an epoxy resin.

8. The endoscope fogging prevention heater apparatus according to claim 1, further comprising a protective film formed in at least part of the surface of the wiring substrate on which the mounting surface is further mounted, except for the surface of the wiring substrate on which the temperature measurement sensor is mounted.

9. An endoscope comprising the endoscope fogging prevention heater apparatus according to claim 1.

10. The endoscope fogging prevention heater apparatus according to claim 1, wherein the conductive element is a lens frame for holding the optical member.

11. The endoscope fogging prevention heater apparatus according to claim 1, wherein the heater is provided adjacent to the temperature measurement sensor in a longitudinal axis direction of the distal end portion.

12. The endoscope fogging prevention heater apparatus according to claim 11, wherein the mounting surface and a circumferential surface of the heater are sealed by the insulator so that the surface of the heater opposite to the mounting surface is free of insulator.

13. The endoscope according to claim 9, further comprising;

an imaging unit having a lens cover;

a lens frame which holds the imaging unit; and wherein the heater is provided on the lens frame.

14. The endoscope fogging prevention heater apparatus according to claim 1, wherein the adhesive is a conductive adhesive.

15. The endoscope fogging prevention heater apparatus according to claim 14, wherein the conductive adhesive is at least thermally conductive.

* * * * *